United States Patent [19]

Dohner

[11] Patent Number: 4,957,704

[45] Date of Patent: Sep. 18, 1990

[54] METHOD OF CORROSION INHIBITION USING HYDROCARBYL POLYCARBOXYLATES COMPOSITIONS

[75] Inventor: Brent R. Dohner, Conroe, Tex.

[73] Assignee: Pennzoil Products Company, Houston, Tex.

[21] Appl. No.: 230,344

[22] Filed: Aug. 9, 1988

[51] Int. Cl.$^5$ .................... C23F 11/00; C07D 307/60
[52] U.S. Cl. ...................... 422/14; 106/270; 106/271; 252/396; 549/252
[58] Field of Search ................ 549/252, 233, 255; 106/270, 271; 252/396; 422/7, 14

[56] References Cited

U.S. PATENT DOCUMENTS

| | | |
|---|---|---|
| 1,151,255 | 8/1915 | Ferguson . |
| 2,529,177 | 11/1950 | Nieland et al. . |
| 2,921,908 | 1/1960 | McCune . |
| 3,193,506 | 7/1965 | Joo . |
| 3,304,348 | 2/1967 | Syrchek . |
| 3,989,637 | 11/1976 | Hogue et al. . |
| 4,209,398 | 6/1980 | Ii et al. . |
| 4,315,863 | 2/1982 | Tomoshige et al. . |
| 4,396,492 | 8/1983 | Bardasz . |
| 4,440,902 | 4/1984 | Diery et al. . |
| 4,612,049 | 9/1986 | Berner et al. . |
| 4,640,793 | 2/1987 | Persinski et al. . |
| 4,696,763 | 9/1987 | Bentley et al. . |
| 4,720,555 | 1/1988 | Nash . |

Primary Examiner—Robert J. Warden
Assistant Examiner—Lyle Alfandary-Alexander
Attorney, Agent, or Firm—Lowe, Price, LeBlanc, Becker & Shur

[57] ABSTRACT

Hydrocarbyl polycarboxylates are formed by the reaction of water and a basic neutralizing agent with a hydrocarbyl poly(succinic anhydride) of the formula R(succinic anhydride)$_x$, wherein R is a hydrocarbyl group derived from a crude or refined hydrocarbon wax having a melting point less than 150° F. and x is an integer of from 3 to 8. The hydrocarbyl polycarboxylates serve as corrosion inhibitors in aqueous compositions.

6 Claims, No Drawings

METHOD OF CORROSION INHIBITION USING HYDROCARBYL POLYCARBOXYLATES COMPOSITIONS

FIELD OF THE INVENTION

The present invention relates to novel hydrocarbon compounds substituted with multiple carboxylate groups which are formed by the reaction of water and a basic neutralizing agent with a hydrocarbyl poly(succinic anhydride). The present invention further relates to corrosion inhibiting compositions and methods employing the novel hydrocarbyl polycarboxylate compounds.

BACKGROUND OF THE INVENTION

Various carboxylate compounds are known in the art for use in inhibiting the corrosion of metal surfaces. For example, carboxylate compounds have been used alone or in combination with other compounds to prevent corrosion of metals in many fields including industrial cooling systems, engine coolants, hydraulic fluids, metalworking fluids and various other applications. Generally, carboxylate compounds are most effective for inhibiting metal corrosion when used in aqueous solutions. Corrosion inhibiting effects result from the binding of the carboxylate anion to the metal or metal oxide surface.

More specifically, monocarboxylates having an alkyl chain have been used for inhibiting corrosion of metals, for example, ferrous metals in aqueous environments. Generally, the longer the alkyl chain included in the monocarboxylate, the greater the corrosion inhibiting effects provided by the monocarboxylate compound. This has a practical limit, however, owing to the solubility of the alkyl group. Monocarboxylates with alkyl chains of greater than 10 to 12 carbon atoms have progressively less water solubility whereby their corrosion inhibiting effects are reduced and their use in many applications is limited. Dicarboxylate compounds have also been used as corrosion inhibitors and generally have been found to be more efficient at reducing corrosion on metal surfaces as compared with monocarboxylate compounds. It is believed that the increased efficiency in corrosion inhibiting effects is attributable to the two functional groups which are available per alkyl group for binding with the metal or metal oxide surface. The effectiveness of dicarboxylate compounds as corrosion inhibitors is increased with increasing alkyl chain length up to about 10 carbon atoms. When the alkyl chain length is greater than about 10 carbon atoms, the molecules begin to function in a manner similar to two monocarboxylates rather than as a dicarboxylate compound.

There is a continuing demand in various industrial fields for compounds and compositions which will inhibit the corrosion of metal surfaces. Additionally, there is a continuing demand for corrosion inhibiting compounds and compositions which provide improved corrosion inhibiting effects as compared with presently used compounds and compositions.

SUMMARY OF THE INVENTION

Accordingly, it is an object of the invention to provide novel hydrocarbon compounds substituted with multiple carboxylate functional groups. It is a further object of the invention to provide novel hydrocarbyl polycarboxylate compounds which are useful as corrosion inhibiting agents. It is an additional object of the invention to provide novel hydrocarbyl polycarboxylate compounds which are water soluble and therefore are particularly useful as corrosion inhibiting agents in aqueous compositions. It is a related object of the invention to provide compositions and methods for inhibiting corrosion of both ferrous and non-ferrous metal surfaces.

These and additional objects are provided by the novel hydrocarbyl polycarboxylate compounds of the present invention. The hydrocarbyl polycarboxylate compounds are formed by the reaction of water and a neutralizing agent with a hydrocarbyl polyanhydride. Preferably, the hydrocarbyl polycarboxylate compounds are formed from the reaction of a hydrocarbyl poly(succinic anhydride) of the formula R(succinic anhydride)$_x$, wherein R is a hydrocarbyl group derived from a crude or refined hydrocarbon wax having a melting point less than 150° F and x is an integer of from 3 to 8. The preferred hydrocarbyl polycarboxylate compounds of the invention are of the formula

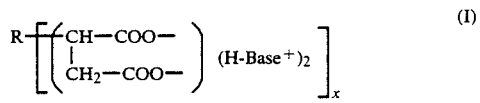

wherein R is a hydrocarbyl group derived from a crude or refined hydrocarbon wax as set forth above, x is an integer of from 3 to 8 and Base comprises a basic neutralizing agent.

The novel hydrocarbyl polycarboxylates of the invention are suitable for use in aqueous compositions, for example, metalworking lubricant compositions, as a corrosion inhibiting agent. The hydrocarbyl polycarboxylate compounds have been demonstrated to inhibit corrosion of both ferrous and, under some conditions, non-ferrous metals.

These and additional objects and advantages will become more apparent in view of the following detailed description.

DETAILED DESCRIPTION

The novel hydrocarbyl polycarboxylates of the present invention are formed by the reaction of water and a basic neutralizing agent with a hydrocarbyl polyanhydride, preferably a hydrocarbyl poly(succinic anhydride). Preferably, the hydrocarbyl poly(succinic anhydride) is of the formula R(succinic anhydride)$_x$, wherein R is a hydrocarbyl group derived from a crude or refined hydrocarbon wax having a melting point less than 150° F and x is an integer of from 3 to 8. The poly(succinic anhydride) of the formula R(succinic anhydride)$_x$ may be formed according to the methods set forth in the commonly assigned Nash U.S. Pat. No. 4,720,555 which is incorporated herein by reference. The expression "hydrocarbyl" refers to a saturated hydrocarbon which may also contain unsaturation, aromatic rings, alkyl aromatics and alicyclic groups, and which has carbon chains which may be straight or branch-chained and which contains at least 6 carbon atoms, and preferably 6 to 100 carbon atoms. The hydrocarbyl groups are derived from hydrocarbons which are soft solids or waxes.

The poly(succinic anhydrides) which are used to prepare the hydrocarbyl polycarboxylates of the present invention have physical and chemical properties which distinguish them from other anhydrides of the prior art. The polyanhydrides are insoluble in the hydrocarbons from which they are made and thus are readily separable therefrom. The anhydrides are not easily describable by specific chemical structure, but rather are complex mixtures of hydrocarbyl, preferably alkyl chains, which contain anhydride groups positioned along the carbon chain. The anhydride groups are attached as discrete units at various positions along the hydrocarbon chain and/or may be linked in multiple units to one another with one or both ends attached to the hydrocarbon. Preferably at least three anhydrides are attached along the hydrocarbon chain.

The hydrocarbyl polyanhydrides from which the hydrocarbyl polycarboxylates of the present invention are produced can be formed from neat hydrocarbons by treating the hydrocarbons with molar excesses of organic anhydride and a peroxide initiator. By the expression "neat hydrocarbons" it is intended to mean that no diluent is necessary for conducting the reaction and that direct reaction can be carried out between the hydrocarbons and the anhydride. The present invention is described herein with reference to the reaction of alkane hydrocarbons with maleic anhydride in order to produce alkyl polysuccinic anhydrides. However, it is to be understood that the invention is inclusive of the use of any long chained hydrocarbon derived from a soft solid as a starting material and any organic anhydride, provided that the polyanhydride products which are produced have the characteristics described herein for producing the hydrocarbyl polycarboxylates.

In preparing the polyanhydrides from which the polycarboxylates of the invention are produced, a molar excess of the anhydride should be reacted with the hydrocarbon. Maleic anhydride is exemplified for conducting the reaction in this application as this is the most readily available anhydride for use. However, equivalent anhydrides could also be used. By the expression "molar excess", it is meant that the molar ratio of anhydride to hydrocarbon for the reaction should be in the range of at least 2:1 and preferably in the range of from about 3:1 to 10:1. It has been found according to the present invention that the use of molar excesses of maleic anhydride increases the conversion of hydrocarbon to a product which is polar in nature and, because of the numerous anyhydride groups, possesses solubility properties and physical properties which distinguish the product from waxy or hydrocarbon soluble succinic anhydrides described in the prior art.

The hydrocarbon starting materials which are reacted with the maleic anhydride are preferably alkyl hydrocarbons and may be branched or straight chained. However, the hydrocarbon chains may also contain unsaturation, aromatic rings, alkyl aromatics, and alicyclic hydrocarbon groups. For example, the hydrocarbons may contain up to about 10 percent by weight of alkyl aromatics. The hydrocarbon reactant in general will have less than 100 carbon atoms and such materials containing 10 to 60 carbon atoms are especially useful. As indicated, the hydrocarbon may be a crude or refined wax (soft solid). Crude wax refers to scale wax, soft wax, footsoil, slack wax, sweat wax or other waxes typically distinguished from refined waxes by their higher oil contents, lower melting points, higher penetration values and sometimes darker colors. Such waxes may be refined by conventional known processes. Refined waxes refer to the various commercial waxes including micro and macro crystalline waxes.

The production of the polyanhydride is carried out by charging the hydrocarbon to a well stirred reactor at atmospheric pressure and bringing the reactor contents to a temperature of about 130–250° C. and more preferably 160–190° C. Good temperature control is important since it has been found that product molecular weight tends to increase with temperature. This is because higher temperatures increase the solubilities of the wax anhydrides and they are thus more likely to have another anhydride unit attach. Thus, narrow temperature control tends to yield more uniform products with respect to the average number of anhydride groups attached to the hydrocarbon. Further, temperatures below 160° tend to favor formation of oligomers of maleic anhydride. The reaction should be conducted under an inert atmosphere for best results. The molten neat anhydride, preferably maleic anhydride, is then added to the hydrocarbon in a dropwise manner until the addition is complete. A free radical generator is added dropwise during the maleic anhydride addition. Any of the known numerous free radical generators may be used, in particular peroxides and hydroperoxides. The amount of free radical generator used should range from about 5 to 15 percent by weight based on the amount of anhydride used in the reaction.

The anhydride and peroxide initiator are typically added over a period of 1 to 3 hours to stirred hydrocarbon maintained within a chosen 5° C. range. Obviously higher volumes would require longer addition times. The addition is then followed by a period of additional stirring and heating, such as 1 to 2 hours for a typical reaction. The stirring and heating are then discontinued, whereupon the crude product settles to the bottom of the reactor leaving molten wax and wax-soluble anhydrides such as an upper layer. This waxy upper layer may be decanted and is suitable for recycle with fresh wax in subsequent batch reactions. The lower phase will be found to harden and may then be ground and extracted with hexane or other aliphatic hydrocarbon to remove wax and wax soluble components. This yields the preferred alkyl polysuccinic anhydride in the form of a fine powder which may be melted and flaked if desired.

The resulting polyanhydride is then reacted with water and a basic neutralizing agent to form the novel hydrocarbyl polycarboxylate compounds of the present invention. Generally, the reaction proceeds as follows:

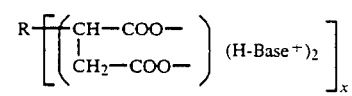

wherein R and x are as defined above and Base comprises the base neutralizing agent. The hydrocarbyl polycarboxylates may be formed by simple blending of the polyanhydride, water and the neutralizing agent. The water and the neutralizing agent should be used in an amount of at least x moles of water and 2x moles of neutralizing agent per mole of polyanhydride of the formula R(succinic anhydride)$_x$ in order to form the hydrocarbyl polycarboxylates of the invention. Thus, each anhydride group contained in the polyanhydride will provide two carboxylate anions in the polycarboxylate compound.

Various neutralizing agents are suitable for use in preparing the polycarboxylate compounds as will be apparent to one of ordinary skill in the art. Generally, any basic compound may be employed. Preferred neutralizing agents include amines and amino alcohols, for example, tertiary amines such as triethanolamine, inorganic hydroxides such as alkali and alkaline earth metal hydroxides and the like. Using a triethanolamine neutralizing agent, the conversion of the polyanhydride to the polycarboxylate would proceed according to the following reaction:

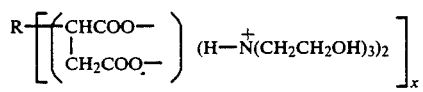

The increased number of carboxylate anions provides enough polarity to make the large molecule water soluble while providing a significant increase in sites available for binding to a metal or metal oxide surface. Hydrocarbyl polycarboxylate compounds have been prepared according to the present invention from both light soft wax poly(succinic anhydride) and heavy soft wax poly(succinic anhydride), the light and heavy designations referring generally to the molecular weight of the hydrocarbon wax.

The hydrocarbyl polycarboxylate compounds of the present invention are suitable for use as corrosion inhibitors. Owing to the water solubility of the polycarboxylate compounds, these compounds are particularly suitable for use as corrosion inhibitors in aqueous compositions. Generally, the amount of hydrocarbyl polycarboxylate compound included in an aqueous composition to provide corrosion inhibiting effects depends on the other components of the composition, the composition of the metal surface on which corrosion is to be inhibited and the environment in which the metal surface is located. However, use of the hydrocarbyl polycarboxylate compounds of the invention in an amount of from 0.01 to about 20 percent by weight of the aqueous compositions generally provide suitable corrosion inhibiting effects. The polycarboxylate compounds may be used in aqueous compositions to prevent corrosion in metalworking lubricants and fluids, industrial cooling systems, engine coolants, hydraulic fluids and the like. As is demonstrated in the following examples, the hydrocarbyl polycarboxylate compounds of the invention provide corrosion inhibiting effects for ferrous metal and, in some conditions, non-ferrous metals such as aluminum and copper.

The following examples demonstrate specific embodiments of the compounds, compositions and methods of the present invention. Unless otherwise specified, percentages are by weight in the examples and throughout the specification.

EXAMPLE 1

This example demonstrates the preparation of hydrocarbyl polycarboxylate compounds according to the present invention by reacting hydrocarbyl poly(succinic anhydride) with water and triethanolamine as the neutralizing agent. A first polycarboxylate, identified as PC-1, was prepared using a polyanhydride of the formula R(succinic anhydride)$_4$ wherein R was derived from a light soft wax. A second polycarboxylate, identified as PC-2, was prepared using a polyanhydride of the formula R(succinic anhydride)$_4$ wherein R was derived from a heavy soft wax. The hydrocarbyl polycarboxylate compounds were prepared by simple blending of the polyanhydride, water and the neutralizing agent. The water was used in an amount of about 4 moles per mole of polyanhydride and the neutralizing agent was used in an amount of about 8 moles per mole of polyanhydride.

The resulting hydrocarbyl polycarboxylate compounds PC-1 and PC-2 were then studied for use in inhibiting corrosion of 1010 carbon steel in a 3.5 weight percent aqueous sodium chloride solution. The carbon steel coupon samples were immersed in the sodium chloride solution containing 0.1 weight percent corrosion inhibitor for one week at room temperature. The corrosion inhibiting effects were measured in terms of weight loss of the carbon steel coupons in the solution. For comparison, similar tests were conducted using carboxylate compounds which are disclosed in the prior art as suitable for inhibiting corrosion of ferrous metal surfaces and which were prepared using triethanolamine as a neutralizing agent. Several commercially available products were also tested for comparison. The results of these corrosion inhibiting tests are set forth in Table I.

TABLE I

| Inhibitor (0.1%) | Stucture | Eq. Wt. | Wt. Loss (mg) |
|---|---|---|---|
| PC-1 (invention) | R(COO$^-$)$_8$ | 240 | 16.9 |
| PC-2 (invention) | R(COO$^-$)$_8$ | 250 | 15.6 |
| Comparative Compounds: | | | |
| Benzoate | C$_6$H$_5$COO$^-$ | 270 | 26.4 |
| t-Butyl Benzoate | 4H$_9$C$_6$H$_5$COO$^-$ | 298 | 29.2 |
| Caprylate | CH$_3$(CH$_2$)$_6$COO$^-$ | 292 | 21.1 |
| Adipate | (CH$_2$)$_4$(COO$^-$)$_2$ | 239 | 33.4 |
| Azelate | (CH$_2$)$_7$(COO$^-$)$_2$ | 260 | 30.2 |
| Sebacate | (CH$_2$)$_8$(COO$^-$)$_2$ | 267 | 30.2 |
| Synkad ® 500 | (Keil Chemicals-neutralized dicarboxylic acid) | 263 | 17.5 |
| Aqualox ® 232 | (Alox Corporation-neutralized dicarboxylic acid) | 250 | 28.2 |

As evidenced by the results set forth in Table I, the polycarboxylate compounds according to the present invention provided substantial corrosion inhibiting effects and significantly improved corrosion inhibition as compared with prior art carboxylate inhibitors.

EXAMPLE 2

The polycarboxylate compounds prepared according to Example 1, namely PC-1 and PC-2, were tested for corrosion inhibiting effects on copper surfaces. The inhibitors were used in an amount of 0.1 weight percent in a 3.5 weight percent aqueous sodium chloride solution in which copper coupons were immersed for one week at room temperature. Corrosion inhibiting effects were measured in terms of weight loss of the copper coupons. The results are set forth in Table II. Since the polycarboxylate derived from the heavy wax, namely PC-2, provided significant corrosion inhibiting effects, this compound was tested repeatedly in order to ensure that the weight loss measurements were accurate.

TABLE II

| Inhibitor (0.1%) | Trial | Wt. Loss (mg) |
|---|---|---|
| None | 1 | 12.0 |
| PC-1 | 1 | 18.8 |
| Synkad ® 500 | 1 | 12.5 |
| PC-2 | 1 | 7.1 |
| PC-2 | 2 | 6.9 |
| PC-2 | 3 | 6.2 |
| PC-2 | 4 | 7.5 |

EXAMPLE 3

The polycarboxylate derived from the heavy soft wax in Example 1, namely PC2, was compared with a commercial copper corrosion inhibitor, Reomet 42 ® supplied by Ciba-Geigy. Since the commercial product is not soluble in a 3.5 percent aqueous sodium chloride solution, this test was run in water of 750 ppm hardness. The copper coupons were immersed in the water containing 0.1 weight percent of a corrosion inhibitor for one week at room temperature. The corrosion inhibiting effects were measured as a percent corrosion reduction based on the corrosion occurring on a copper coupon immersed in the hard water which did not contain any corrosion inhibitor. The results are set forth in Table III.

TABLE III

| Inhibitor (0.1%) | % Corrosion Reduction |
|---|---|
| Reomet ® 42 | 95 |
| PC-2 | 46 |

The results set forth in Table III demonstrate that while PC-2 is not as efficient as the commercially available copper corrosion inhibitor, the hydrocarbyl polycarboxylate of the invention does provide significant corrosion inhibiting protection to copper surfaces.

EXAMPLE 4

The polycarboxylate compounds prepared in Example 1 were also studied for their corrosion inhibiting effects in acidic environments. Specifically, the corrosion inhibiting effect of 0.1 weight percent of the compounds on 1010 carbon steel, copper and aluminum samples immersed in a 0.1 N HCl for one week at room temperature were studied. The corrosion inhibiting effects were measured as a percent corrosion reduction compared with samples immersed in the acidic solutions which did not contain a corrosion inhibitor. The results of these studies are set forth in Table IV and demonstrate that the polycarboxylates of the invention inhibit corrosion on both ferrous and non-ferrous metals in an acidic environment.

TABLE IV

| Metal | Inhibitor (0.1%) | % Corrosion Reduction |
|---|---|---|
| Steel | PC-1 | 78% |
|  | PC-2 | 78% |
| Copper | PC-1 | 72% |
|  | PC-2 | 88% |
| Aluminum | PC-1 | 84% |
|  | PC-2 | 80% |

The preceding examples are set forth to illustrate specific embodiments of the invention and are not intended to limit the scope of the compositions and methods of the present invention. Additional embodiments and advantages within the scope of the claimed invention will be apparent to one of ordinary skill in the art.

What is claimed is:

1. A method for inhibiting corrosion on a metal surface, comprising contacting the metal surface with an aqueous solution including a corrosion inhibitor comprising a hydrocarbyl polycarboxylate compound formed by the reaction of water and a neutralizing agent with a hydrocarbyl poly(succinic anhydride) of the formula R(succinic anhydride)$_x$, wherein R is a hydrocarbyl group derived from a crude or refined hydrocarbon wax having a melting point less than 150° F and x is an integer of from 3 to 8.

2. A method as defined by claim 1, wherein said aqueous solution includes said corrosion inhibitor in an amount of from about 0.01 to about 20 percent by weight.

3. A method as defined in claim 1, wherein said surface comprises a ferrous metal.

4. A method as defined by claim 1, wherein said surface comprises a non-ferrous metal.

5. A method for inhibiting corrosion on a metal surface, comprising contacting the metal surface with an aqueous solution including a corrosion inhibitor comprising a hydrocarbyl polycarboxylate compound of the formula

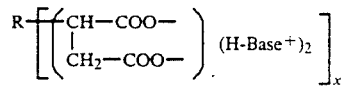

wherein R is a hydrocarbyl group derived from a crude or refined hydrocarbon wax having a melting point less than 150° F, x is an integer of from 3 to 8, and Base represents a basic neutralizing agent.

6. A method as defined by claim 5, wherein said aqueous solution includes said corrosion inhibitor in an amount of from about 0.01 to about 20 percent by weight.

* * * * *